United States Patent [19]

Smith

[11] Patent Number: 4,634,042
[45] Date of Patent: Jan. 6, 1987

[54] METHOD OF JOINING REFRACTORY METALS TO LOWER MELTING DISSIMILAR METALS

[75] Inventor: Kevin Smith, Miami, Fla.

[73] Assignee: Cordis Corporation, Miami, Fla.

[21] Appl. No.: 598,879

[22] Filed: Apr. 10, 1984

[51] Int. Cl.⁴ .............................................. B23K 31/00
[52] U.S. Cl. .................... 228/173.4; 228/254
[58] Field of Search ................ 228/173 E, 254, 174; 604/164, 170; 128/657

[56] References Cited

U.S. PATENT DOCUMENTS

| | | | |
|---|---|---|---|
| 1,614,501 | 1/1927 | Stoekle . | |
| 2,258,836 | 10/1941 | Willner | 228/254 |
| 2,387,903 | 10/1945 | Hensel | 219/4 |
| 2,922,092 | 1/1960 | Gazzara et al. | 317/234 |
| 3,006,065 | 10/1961 | Watson | 228/254 |
| 3,079,676 | 3/1963 | Meyers | 29/194 |
| 3,159,462 | 12/1964 | Kadelburg | 29/195 |
| 3,412,458 | 11/1968 | Delnero | 228/178 |
| 3,521,620 | 7/1970 | Cook | 604/170 |
| 3,547,103 | 12/1970 | Cook | 604/170 |
| 3,812,393 | 5/1974 | Koo et al. | 445/48 |
| 3,877,495 | 4/1975 | Koo et al. | 140/71.5 |
| 3,906,938 | 9/1975 | Fleishhacker | 604/170 |
| 4,003,369 | 1/1977 | McCarty et al. | 128/2 M |
| 4,080,706 | 3/1978 | Heilman et al. | 29/173 |
| 4,291,444 | 9/1981 | Heilman et al. | 29/25.14 |

Primary Examiner—Nicholas P. Godici
Assistant Examiner—G. Reid
Attorney, Agent, or Firm—Henry W. Collins; Thomas R. Vigil

[57] ABSTRACT

The method for manufacturing an angiographic coil spring guidewire includes the step of: coating a predetermined length of a refractory metal wire with a metallic glaze which has a melting point less than the refractory metal wire; wrapping the coated wire around a mandrel in order to form a wire coil therearound; removing the mandrel from the wire coil; inserting a core wire having a melting point less than the wire coil and close to the melting point of the metallic glaze within the wire coil, so that a portion of the core wire protrudes from one end of the wire coil; surrounding the wire coil and core wire except for the protruding end of the core wire with a thermally conductive chill; heating the portion of the core wire which protrudes from the wire coil until the core wire melts so that a rounded head portion is formed such that the heat from the core wire melts the metallic glaze on the inside surface of the wire coil in order to create an oxide-free resilient bond between the inside surface of the wire coil and the core wire.

14 Claims, 8 Drawing Figures

U.S. Patent  Jan. 6, 1987  4,634,042
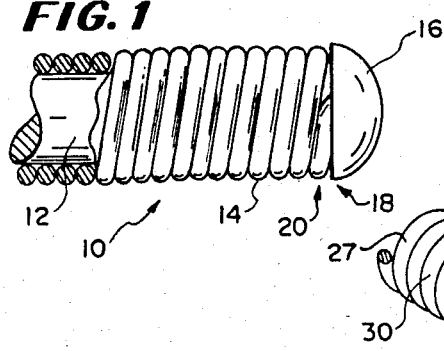
FIG. 1
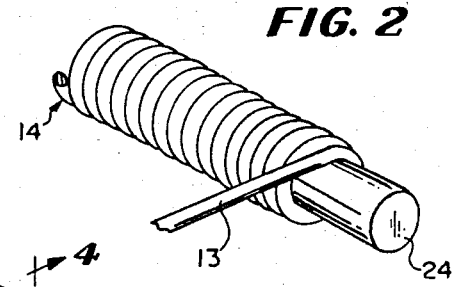
FIG. 2
FIG. 3
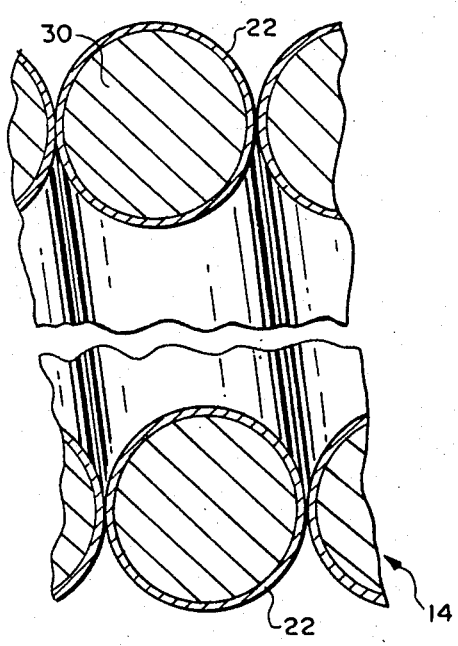
FIG. 4
FIG. 5
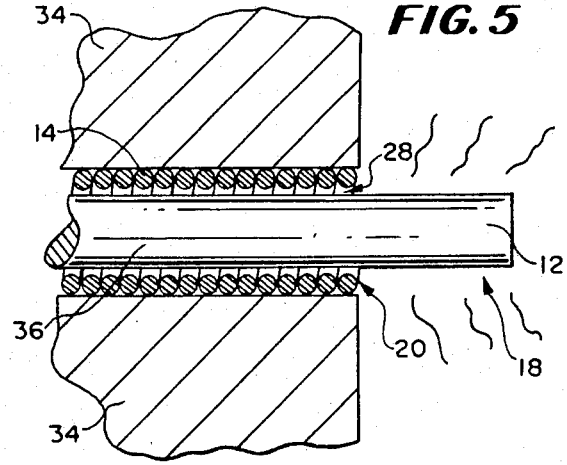
FIG. 6
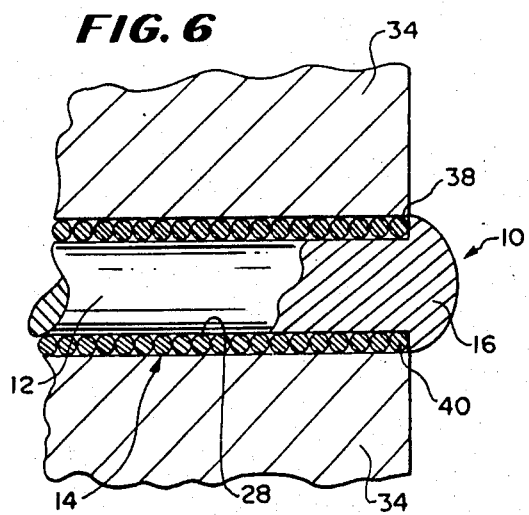
FIG. 7
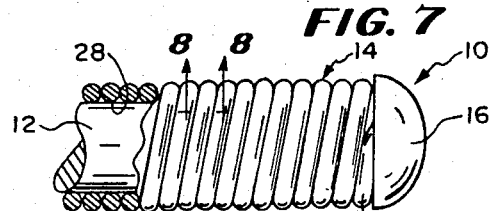
FIG. 8
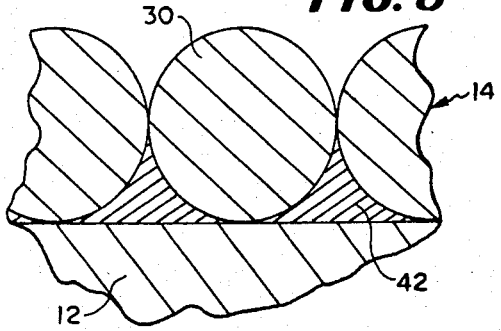

METHOD OF JOINING REFRACTORY METALS TO LOWER MELTING DISSIMILAR METALS

BACKGROUND OF THE INVENTION

1. Field of the Invention

The present invention relates to a method for manufacturing an angiographic coil spring guidewire for use with a catheter for guiding the catheter into a vessel of a body. The guidewire is made by joining a stainless steel core wire to a refractory metal wire coil wrapped therearound by first coating the refractory metal wire coil with a noble metal glaze and then melting the glaze to create an oxide-free resilient bond between the wire coil and the core wire.

2. Description of the Prior Art

Heretofore, various methods for joining dissimilar metals for the manufacture of various devices which require metallic bonds or joints have been proposed. Examples of such previously proposed methods are disclosed in the following U.S. patents:

| U.S. PAT. NO. | PATENTEE |
| --- | --- |
| 1,614,501 | Stoekle |
| 2,387,903 | Hensel |
| 2,922,092 | Gazzara et al |
| 3,079,676 | Meyers |
| 3,159,462 | Kadelburg |
| 3,877,495 | Koo et al |
| 4,291,444 | McCarty et al |

The Stoekle U.S. Pat. No. 1,614,501 discloses a method of uniting tungsten and iron by forming a permanent intermediate bond therebetween with an alloy of copper and nickel by various methods of welding known to the art.

The Hansel U.S. Pat. No. 2,387,903 discloses the manufacture of an electrical contact assembly by brazing or otherwise attaching contact facing discs or similar parts made from hard or refractory metals or compositions, such as tungsten or the like, to an intermediary backing member made of molybdenum which has a coefficient of expansion substantially the same as tungsten and which is adapted to substantially eliminate or minimize the surface stresses set up in the contact face. The bimetallic body manufactured in this way may then be attached to a primary backing member such as a steel rivet, a screw, an armature blank, a lever arm, or a welding electrode by brazing or welding.

The Gazzara et al U.S. Pat. No. 2,922,092 discloses a base contact member for use in a semi-conductive device, wherein the base contact member is adapted to be soldered to a base mount. The base contact member comprises a body of a metal selected from the group consisting of tantalum, tungsten and base alloys thereof having a coefficient of thermal expansion approaching that of silicone, and which have applied thereto a thin coating of a metal selected from the group consisting of gold, platinum and rhodium.

The Meyers U.S. Pat. No. 3,079,676 discloses a method of uniting high melting point metal parts with other high melting point metal parts or, in the alternative, uniting high melting point metal parts with metal parts having a lower melting point. Such method is particularly adapted for the manufacture of vacuum tubes. A gold-copper-cobalt brazing composition is used to join two metals, such as tungsten, in order to provide a strong brazing joint therebetween.

The Kadelburg U.S. Pat. No. 3,159,462 discloses a method for securing a contact, such as a tungsten contact, to a semi-conductor element, such as a silicone wafer, by a gold-boron solder. A nickel plated tungsten contact wafer is heated in the presence of the gold-boron alloy composition in a vacuum at temperatures greater than 1000° C., placed intermediate a silicone semi-conductor wafer in a copper base therefor, and then soldered to the silicone wafer and the copper base with a gold-rhenium solder.

The Koo et al U.S. Pat. No. 3,988,495 discloses a method for manufacturing an annealed tungsten filament wire for electric lamps with a reduced amount of impurities. A filament of wire, preferably tungsten, is coated with copper and wound around a mandrel and annealed at a temperature greater than 1000° C. The mandrel and coil are then cooled to room temperature, cut into desired lengths, and the mandrels are dissolved from the coils.

The McCarty et al U.S. Pat. No. 4,291,444 discloses an improved process of manufacturing a tungsten lamp filament in which a tungsten wire is wrapped around a wire mandrel having a central core of molybdenum and further coated with tantalum or tungsten and then heated to at least 1600° C. The mandrel is then removed from the coiled tungsten filament by immersing the coil and mandrel in a known or modified acid mixture.

As will be described in greater detail hereinafter, the method of the present invention for manufacturing an angiographic guidewire differs from the various methods of joining metals to each other previously proposed by providing an oxide-free, resilient braze-like bond between a stainless steel core wire and a refractory metal wire coil wound therearound. By providing an oxide-free bond between the two metals, an angiographic guidewire manufactured according to the teachings of the present invention does not contain brittle bonding joints and thereby permits the guidewire to be freely manipulated through a vessel of a body.

SUMMARY OF THE INVENTION

According to the present invention, there is provided an angiographic coil spring guidewire adapted to be used in connection with a catheter in order to guide the catheter into a vessel of a body, said guidewire comprising a core wire, a length of refractory metal wire wrapped around said core wire and forming a wire coil therearound, said core wire being bonded to said refractory metal wire coil by an oxide-free resilient metallic bond.

Further, according to the invention, there is provided a method for manufacturing an angiographic coil spring guidewire for use with a catheter for guiding the catheter into a vessel of a body, including the steps of: coating a predetermined length of wire having a high melting point with a metallic glaze having a melting point less than said wire; wrapping said coated wire around a mandrel to form a wire coil therearound; removing said mandrel from said wire coil; inserting a core wire within said wire coil so that a portion of said core wire protrudes from one end of said wire coil, said core wire having a melting point which is less than said wire coil and which is close to the melting point of said metallic glaze; surrounding said wire coil with a thermally conductive chill; heating said protruding portion of said core wire until said core wire melts such that said metallic glaze also melts in order to provide an oxide-free resilient bond between said wire coil and said core wire.

BRIEF DESCRIPTION OF THE DRAWINGS

FIG. 1 is a side view of an angiographic coil spring guidewire with a portion thereof broken away.

FIG. 2 is a perspective view of a length of metallically plated wire wrapped around a mandrel.

FIG. 3 is a perspective view of a wire coil formed after the length of wire had been wrapped around the mandrel shown in FIG. 2, and shows the mandrel removed from the wire coil.

FIG. 4 is a sectional view of the wire coil shown in FIG. 3 and is taken along line 4—4 of FIG. 3.

FIG. 5 is a sectional view of the wire coil with a core wire therein surrounded by a thermally conductive chill with a portion of the core wire protruding from the wire coil and the chill in accordance with the teachings of the present invention.

FIG. 6 is a sectional view of the wire coil and the core wire surrounded by the thermally conductive chill after the protruding portion of the wire core has been melted to form an angiographic guidewire.

FIG. 7 is a side view of a portion of the angiographic guidewire with portions broken away after it has been removed from the thermally conductive chill.

FIG. 8 is a sectional view of the angiographic guidewire and is taken along line 8—8 of FIG. 7.

DESCRIPTION OF THE PREFERRED EMBODIMENTS

Referring now to FIG. 1, there is illustrated therein an angiographic guidewire 10 which is constructed according to the teachings of the present invention and which is adapted for use with a catheter for guiding the catheter into a vessel of a body. The guidewire 10 includes a stainless steel core wire 12 and a wire 13 which is wrapped around the core wire 12 and which is metallically bonded to the core wire 12 to form a wire coil 14 around the core wire 12.

The angiographic guidewire 10 further includes a rounded head portion 16 which is located at a distal end 18 of the core wire 12 and which is situated adjacent to and against a distal end 20 of the wire coil 14. As will be described in greater detail hereinafter, the rounded head portion 16 of the core wire 12 is formed by heating the distal end 18 of the core wire 12, until it melts to form the head portion 16.

Referring now to FIG. 2, the wire coil 14 of the guidewire 10 is formed from a predetermined length of the wire 13 preferably having a diameter of 0.003 inch. The wire 13 is made of a refractory metal, preferably tungsten, although other refractory metals, as tantalum or rhenium, can be used.

The wire 13 is first plated with a noble metal 22 (FIG. 4), preferably gold, in order to encase, preserve and protect an oxide-free surface of the refractory metal wire 13. Although gold is used in the preferred embodiment of the present invention, other noble metals, such as platinum or rhodium, can be used to coat the wire 13.

Noble metals are chosen to coat the wire 13 since the melting points of noble metals are significantly lower relative to the melting points of refractory metals, as will be discussed in greater detail hereinafter.

Once the wire 13 has been plated with the noble metal 22 to a thickness of approximately 5–10 microns around the wire 13, the wire 13 is cooled to room temperature and wrapped around a mandrel 24 in order to form the wire coil 14 therearound. The mandrel 24 has a specific outer diameter so that when the mandrel 24 is removed from the wire coil 14, the inner surface 26 of the wire coil 14 defines a hollow core or lumen 28. The inner diameter of the wire coil 14 is preferably 0.011 inch.

Since the wire 13 is plated with a noble metal 22 prior to the formation of the wire coil 14 around the mandrel 24, the wire coil 14 has a coating of the noble metal 22 on both its inner surface 26 and outer surface 27, as well as between each of the turns 30 of the wire coil 14.

In order to provide strength and resilient flexibility to the wire coil 14, the stainless steel core wire 12 is inserted within the hollow core 28 of the wire coil 14 so that the distal end 18 of the core wire 12 protrudes from the distal end 20 of the wire coil 14 a distance equal to twice the diameter of the core wire 12, or about 0.020 inch.

Referring now to FIG. 5, the metallic bonding process of joining the core wire 12 to the wire coil 14 occurs within a thermally conductive copper chill 34 which surrounds the wire coil 14 and the core wire 12, except for the distal end 18 of the core wire 12 which protrudes from the wire coil 14 and from the copper chill 34.

The copper chill 34 allows the distal end 18 of the core wire 12 to be melted by a flame or arc, while at the same time, preventing the remaining portion 36 of the core wire 12 within the wire coil 14 and the copper chill 34 from melting by conducting the heat away from the core wire 12. In this manner, the amount of the core wire 12 that is to be melted can be controlled by varying or adjusting the length of the portion of the distal end 18 of the core wire 12 which protrudes from the wire core 14 and the copper chill 34.

Furthermore, since the melting point of tungsten is 3410° C., and the melting point of gold is 1064° C., and the melting point of stainless steel is similar to the melting point of gold or other noble metals, the temperature to which the core wire 12 is heated does not approach the melting point of tungsten, so that the wire coil 14 does not melt and does not interfere with the metallurgy of the stainless steel core wire 12.

As previously stated above, the distal end 18 of the core wire 12 is heated with an arc or flame to a temperature at which the stainless steel core wire 12 becomes molten. The molten steel of the heated distal end 18 of core wire 12 flows within the distal end 20 of the wire coil 14 by capilliary action with a portion of the melted core wire 12 forming the rounded head portion 16 of the guidewire 10, as illustrated by FIGS. 6 and 7. As the molten distal end 18 of the core wire 12 flows within the distal end 20 of the wire coil 14, the head 16 is formed adjacent the distal end 20 of the wire coil 14 with a shoulder 38 of the head 16 being formed against and bonded to an outer turn 40 of the wire coil 14.

When the heat of the steel core wire 12 is conducted to the noble metal 22 plated around the wire coil 14, the noble metal 22 either dissolves or melts. The melted or dissolved noble metal 22 then exposes the clean, oxide-free surface of the wire coil 14 on the outside of the wire coil 14 and bonds the oxide-free inside surface 26 of the wire coil 14 to the core wire 12 before oxidation of the refractory metal from which the wire coil 14 is made can take place. FIG. 8 illustrates such a glaze-like resilient bond 42 which is formed between the inside surface 26 of the wire coil 14 and the core wire 12.

It is apparent that one of the advantages of manufacturing the angiographic guidewire 10 according to the method described above is that low temperatures, relative to the melting point of the refractory metal of the wire coil 14, are used to melt the core wire 12 so that the refractory metal is not melted and thereby interference with the metallurgy of the stainless steel core wire 12 is prevented. Since refractory metals generally form brittle intermetallic compounds with other metals, which, when present at a joint interface, would render the joints brittle with little or no strength or corrosive resistance, the method of joining the wire coil 14 to the core wire 12 according to the teachings of the present invention, provides an angiographic guidewire 10 which has resilient strength for manipulation of the guidewire into a vessel of a body in order to guide a catheter into the vessel of the body.

Furthermore, formation of the head 16 of the guidewire 10 from the core wire 12 provides a smooth tip for facilitating the manipulation of the guidewire 10 into the vessel of the body, as well as eliminating an additional step of attachment of a head 16 to the core wire 12 and the wire coil 14.

From the foregoing description, it will be apparent that the method of joining a stainless steel core wire 12 to a refractory metal wire coil 14 previously plated with a noble metal 22, according to the teachings of the present invention, has a number of advantages, some of which have been described above and others of which are inherent in the invention.

Also, it will be apparent that modifications can be made to the method without departing from the teachings of the present invention.

Accordingly, the scope of the invention is only to be limited as necessitated by the accompanying claims.

I claim:

1. A method for manufacturing an angiographic coil spring guide wire for use with a catheter for guiding the catheter into a vessel of a body, including the steps of: coating a predetermined length of wire having a high melting point with a metallic glaze having a melting point less than said wire; wrapping said coated wire around a mandrel to form a wire coil therearound; removing said mandrel from said wire coil; inserting a core wire within said wire coil so that a portion of said core wire protrudes from one end of said wire coil, said core wire having a melting point which is less than said wire coil and which is close to the melting point of said metallic glaze; surrounding said wire coil with a thermally conductive chill; heating said protruding portion of said core wire until said core wire melts such that said metallic glaze also melts in order to provide an oxide-free resilient bond between said wire coil and said core wire.

2. The method of claim 1 wherein said wire coil is made of a refractory metal.

3. The method of claim 2 therein said refractory metal is selected from the group comprising tungsten, tantalum or rhenium.

4. The method of claim 1 wherein said metallic glaze is a noble metal.

5. The method of claim 4 wherein said noble metal is selected from the group comprising gold, platinum or rhodium.

6. The method of claim 1 wherein said core wire is stainless steel.

7. The method of claim 6 wherein said stainless steel core wire has an outer diameter which is almost equal to the inner diameter of said wire coil.

8. The method of claim 7 wherein said outer diameter of said stainless steel core wire is 0.010 inch.

9. The method of claim 7 wherein said inner diameter of said wire coil is 0.011 inch.

10. The method of claim 1 wherein said stainless steel core wire protrudes from said wire coil a distance equal to approximately twice the diameter of said core wire.

11. The method of claim 1 wherein said thermally conductive chill is a copper chill.

12. The method of claim 1 wherein said wire coil is coated with said noble metal to a thickness of approximately 5-10 microns.

13. The method of claim 1 wherein said core wire is approximately 0.003 inch thick.

14. The method of claim 1 including the step of forming a head member, said head member being formed from said protruding portion of said core wire upon melting of said protruding portion of said core wire, said head member having a rounded configuration and being situated against said one end of said wire coil.

* * * * *